(12) United States Patent
Poris et al.

(10) Patent No.: US 6,925,860 B1
(45) Date of Patent: Aug. 9, 2005

(54) LEVELING A MEASURED HEIGHT PROFILE

(75) Inventors: Jaime Poris, Boulder Creek, CA (US); Claudio L. Rampoldi, Mountain View, CA (US)

(73) Assignee: Nanometrics Incorporated, Milpitas, CA (US)

( * ) Notice: Subject to any disclaimer, the term of this patent is extended or adjusted under 35 U.S.C. 154(b) by 243 days.

(21) Appl. No.: 10/370,912

(22) Filed: Feb. 21, 2003

(51) Int. Cl.[7] .............................................. G01N 21/00

(52) U.S. Cl. ......................................... 73/105; 73/1.79

(58) Field of Search ................... 73/1.79, 105; 33/556, 33/548; 356/27, 28.5, 496, 511, 516, 600; 702/155, 166, 167, 168

(56) References Cited

FOREIGN PATENT DOCUMENTS

JP           2000-260840          9/2000    ............ H01L 21/66

*Primary Examiner*—Robert Raevis
(74) *Attorney, Agent, or Firm*—Silicon Valley Patent Group LLP

(57) ABSTRACT

The height profile of a sample that includes at least one film on a substrate is leveled based on the measured thickness of the overlying film. An apparatus that levels the height profile includes a metrology tool that generates the height profile of a sample and a metrology tool that measures the thickness of one or more layers of a film stack on top of a substrate at two or more locations. The measured thickness is then used to level the height profile to reduce any tilt error before a step height calculation is made. For example, the slope of the thickness between two or more measurement points may be used to adjust the height profile. Once the height profile is leveled, step heights may be calculated with reduced tilting error.

20 Claims, 4 Drawing Sheets

LEVELING A MEASURED HEIGHT PROFILE

FIELD OF THE INVENTION

The present invention relates to accurately measuring a height profile of a sample, and in particular to leveling the tilt of the measured height profile of the sample.

BACKGROUND

The height profile of a sample, such as a semiconductor substrate, flat panel display, or similar substrates, can be used to determine, e.g., surface roughness, surface curvature, or shape and/or step heights associated with features on the surface of the sample. In the semiconductor industry, for example, it is desirable to measure the height of a step on the surface of the substrate at various times during processing. The height profile of a sample can be conventionally measured in many different ways, such as a single point measurement system, e.g., a contact profilometer or atomic force microscope (AFM), or multiple point measurement system, e.g., a differential interferometer.

One source of error in the measurement of the height profile of features on a sample is caused by tilting. Tilting refers to a constant slope imposed onto a measured height profile, as opposed to an arbitrary shape with a non-zero second derivative (which indicates curvature) imposed onto the height profile.

When determining step heights from a measured height profile, tilting of the sample may result in significant step height errors that are related to the slope of the tilted, measured height profile and the lateral distance over which the profile is measured. FIGS. 1, 2A, and 2B show a level step height profile 10, a tilted step height profile 20, and another titled step height profile 30, respectively. As shown in FIG. 1, the height of step 11, which is $h_0$, is calculated as the vertical distance between points 12 and 14 on the level height profile 10. FIG. 2A, on the other hand, shows that the height of step 21, which is actually $h_0$, is significantly different than step height $h_1$, which is calculated as the vertical distance between points 22 and 24 on the tilted step height profile. FIG. 2A overestimates the height of the step, i.e., $h_0$ is less than $h_1$. FIG. 2B shows an alternative choice for measurement locations 32 and 34 that underestimates the height of the step 31, i.e., $h_0$ is greater than $h_1$. For a tilted height profile, increasing the lateral separation between the two points chosen to determine the step height results in an increased over or under estimation of the step height. Thus, as can be seen, it is imperative to level the height profile of a sample prior to calculating step heights from the height profile. Failure to level will result in a significant over or under estimation of the true step height.

All single point measurement techniques are susceptible to tilting errors due to the imperfect alignment of the metrology tool with the sample. For example, a contact profilometer will display tilting errors when a step on a silicon wafer is scanned. This is caused by the lack of orthogonality of the metrology head (the stylus and vertical height measuring system in a profilometer) to the sample. The flatness of the substrate, the thickness variation across the substrate and the flatness of the chuck that holds the wafer can also contribute to tilting errors. An AFM also exhibits tilting errors due to its single measurement point procedure.

A recent trend in semiconductor processing is to hold a 300 mm diameter silicon substrate by the edges instead of contacting the back of the wafer with a flat, vacuum chuck, in an attempt to minimize contamination of the wafer. Gravitational forces can cause over 100 microns of sagging of the wafer from the edge to the center, which results in another source for (variable) tilting of the wafer. Over small distances, e.g., $200\mu$, sagging appears as a tilt error with the degree of tilting varying from the center to the edge of the wafer. Over large distances, e.g., $1000\mu$, sagging appears as curvature.

Conventionally, a contact profilometer or an AFM can level a measured height profile by choosing two locations on the measured height profile that are assumed to be at the same height. Typically, the operator must choose the desired two locations. The software then levels the plot based on these chosen locations. Two more locations on the measured height profile are then chosen to calculate the step height. This procedure can also be executed automatically by designating two positions for leveling and two positions for the step height calculation within a recipe before the measurement is made. The software then levels the plot and calculates the step height automatically. The software is also capable of taking an average over a designated segment of the scan for these four values which generally improves the precision of the measurement. Unfortunately, the tilting related error may still be significant if there are no flat regions or flat regions cannot be properly identified on the height profile.

A differential interferometer is capable of generating a height profile in two different types of scans; a referential scan, which does not need to be corrected for tilting, and a differential scan. In general, a laser differential interferometer projects two laser spots onto the sample surface at two points and scans the two spots across the sample to generate a multitude of measurement points. A height difference between the points on the sample surface causes a difference in the path length between the two beams, which results in a phase difference between the two beams. The measured phase difference can be converted into a step height difference between the two spots with knowledge of the laser wavelength. Typically, an entire line scan is made generating the height profile associated with the scanned area. When collecting the raw data, the sample can be translated with respect to the measurement tool or the measurement tool can be translated with respect to the sample.

In a referential scan, one laser spot acts as a reference and is scanned across a flat region of the sample, while the second laser spot traverses the area of interest. The reference spot compensates for any tilting that may occur in any direction relative to the scan direction because both spots are subjected to the same amount of tilting. Thus, step heights can be accurately and precisely determined from the generated height profile in a referential scan without requiring tilt correction. Typically, even if the metrology tool is perfectly orthogonal to the sample surface, there is also a measured non-zero phase shift between the two spots caused by slight path differences of the two beams in the metrology device. Nevertheless, this error is added to every point of a referential scan and does not impact a step height calculation. For most situations, if the sample exhibits curvature, which often occurs for very long scans, e.g., exceeding 1000 microns, on a semiconductor wafer, a referential scan will not correct the curvature.

In a differential scan, the two spots are closely spaced and follow the same path, with one spot slightly ahead of the other spot. For example, the spot size can be 3 microns and the spacing of the two spots can be 4.5 microns center to center. The profile generated from this plot is not the height profile but the first derivative of the height profile, i.e., the slope of the height profile. Unlike the profile produced by a referential scan, the slope of the height profile produced by a differential scan is susceptible to tilting errors even though two spots are employed. For example, in a flat region of a scan, typically non-zero values of the slope of the height profile are measured due to both tilting of the sample with respect to the metrology device as well as the intrinsic phase shift due to the slight difference in path length traversed by both spots.

One known method used to eliminate tilting error in a differential scan is to always start the scan in a region of the sample that is known to be very flat (or identify a region of the scan that is known to be very flat). The measured value of the slope of the height profile of the flat region of the scan is then subtracted from the remainder of the slope of the height profile data. The flat regions of the scan (regions of the scan that have the same values as the initial part of the scan) will then exhibit a value of zero for the slope of the height profile. When this slope of the height profile data is integrated, the height profile is generated without tilting errors.

Unfortunately, if the scan starts in a region of the sample that is not flat or a flat location along the scan is not known, this procedure will not work. Due to limitations associated with the geometries of features on the surface of typical samples, such as semiconductor wafers, it is not always possible to choose a flat region to start a scan or identify a flat region of the scan. This is particularly true when the measurement procedure is automated and it is desirable to execute the measurements without further human intervention.

Accordingly, there remains a need to accurately level a height profile measurement produced by differential scans of a differential interferometer as well as single point metrology systems to eliminate tilting errors.

SUMMARY

The height profile of a sample that includes at least one film on a substrate is leveled based on the measured thickness of the overlying film at two or more locations, in accordance with the present invention. In one embodiment of the present invention, a method includes determining a height profile of a sample, which includes a substrate with at least one overlying film. The thickness of the overlying film is measured at a plurality of locations. The tilt of the height profile is then adjusted using the measured thickness of the overlying film. In one embodiment, the method includes determining the slope between the plurality of measurement locations based on the measured thickness and distance between the plurality of measurement locations. The adjustment to the tilt of the height profile uses the determined slope. The height profile of the sample may be generated in various manners, such as through the use of a single point measurement tool. Alternatively, a differential interferometer may use a differential scan to generate the slope of the height profile, which is then integrated to determine the height profile of the sample.

In another embodiment of the present invention, an apparatus includes a first metrology tool that measures either the height profile or the slope of the height profile of a sample that includes at least one film overlying a substrate. The apparatus also includes a second metrology tool that measures the thickness of the at least one film at a plurality of locations. A computer system is coupled to the first metrology tool to receive signals indicating the height profile or the slope of the height profile of the sample. The computer system is also coupled to the second metrology tool to receive signals indicating the thickness of the film being measured at each of the plurality of locations. The computer system has a computer-usable medium having computer-readable program code embodied therein for adjusting the height profile of the sample based on the measured thickness between the plurality of locations. In one embodiment, there is computer-readable program code for determining the slope of the thickness between the plurality of locations based on the measured thickness and distance between the plurality of locations, wherein adjusting the height profile of the sample is based on the slope of the thickness. Where the slope of the height profile is measured by the first metrology tool, the computer-readable program code is also for integrating the slope of the height profile to generate the height profile.

The first metrology tool may be, e.g., a contact profilometer, an atomic force microscope, or a differential interferometer. The second metrology tool may be, e.g., a reflectometer, an ellipsometer, an x-ray diffraction tool, and a resistivity measurement tool.

DETAILED DESCRIPTION

The present invention relates to accurately leveling a measured height profile of a sample to minimize tilting errors before a step height calculation is made. Conventional methods of correcting tilting in a differential scan or a single point scan typically rely on the existence of known flat locations on the sample. However, non-uniformities and normally occurring variations in the sample may create errors when conventional correcting methods are used.

Figure 1:
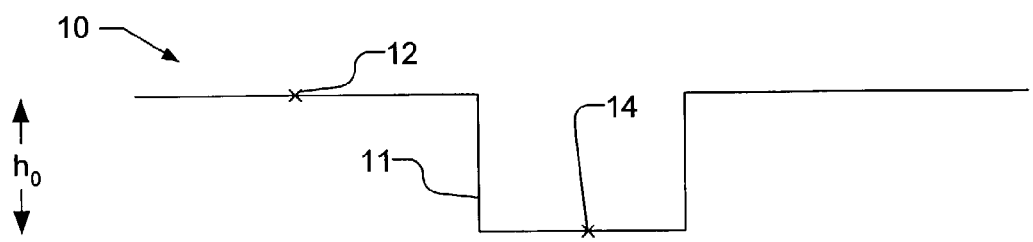
FIG. 1 shows a level step height profile.
Figure 2A:
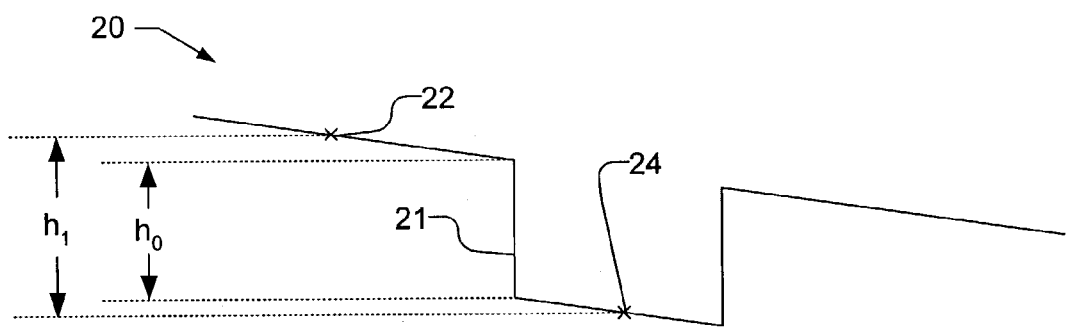
FIGS. 2A and 2B show tilted step height profiles.
Figure 2B:
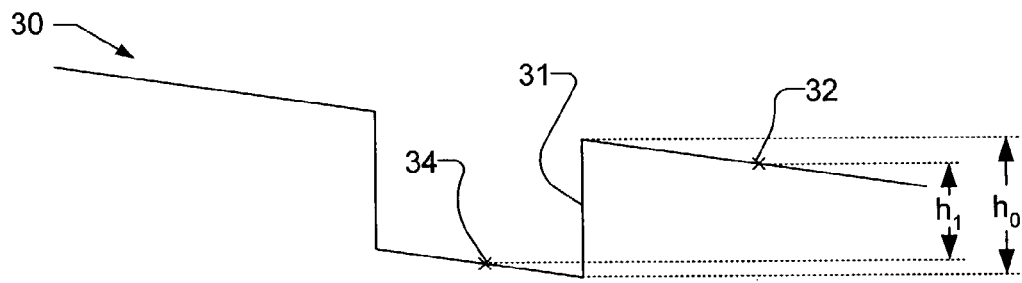
Figure 3:
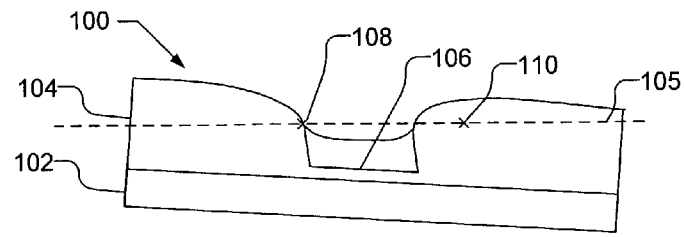
FIG. 3 shows a side view of a sample with a tilting error.

By way of example, FIG. 3 shows a side view of a sample 100, in which there is a tilting error. Sample 100 includes a substrate 102 and an overlying film 104 that includes a step 106. The thickness non-uniformity of film 104 in the vicinity of the step can create errors when the sample 100 is conventionally leveled. For example, sample 100 includes two presumed flat measurement points 108 and 110. Location 110 is an adequate measurement point, whereas location 108 is chosen too close to the step 106 and is not at the same height as location 110. When the sample 100 is leveled based on the heights of measurement points 108 and 110, as indicated by broken line 105, the underlying thicknesses of points 108 and 110, which are different, will produce an error when the sample 100 is leveled. As shown in FIG. 3, the measurement points 108 and 110 are adjusted to be at the same height, but as can be seen, substrate 102 and a majority of the top of film 104 are significantly tilted. It should be understood, of course, that the leveling of sample 100 is typically performed mathematically, but is shown schematically in FIG. 3 for illustrative purposes.

Figure 4:
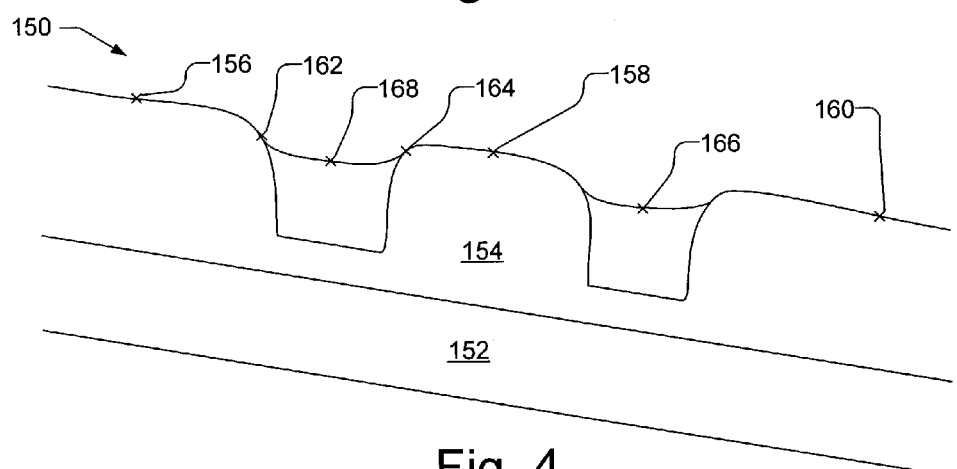
FIG. 4 shows a side view of a tilted height profile with non-flat regions of a thin film over a flat substrate.

FIG. 4 shows a tilted height profile 150 with non-flat regions of a thin film 154 over a flat substrate 152. Locations 156, 158, and 160 would be good choices to use for conventional leveling or for locations to measure the thickness. Locations 162 and 164 would be poor choices to use for conventional leveling, but would be acceptable for measuring the thickness. Ideally, the thickness should be measured in areas with the least slope to minimize errors associated with the location of the thickness measurement points. One advantage of the proposed procedure is that the two measurement locations need not be at the same height allowing much more freedom when automating the measurement. Locations 166 and 168 would be good choices to measure the lower part of the steps.

Figures 5A, 5B:
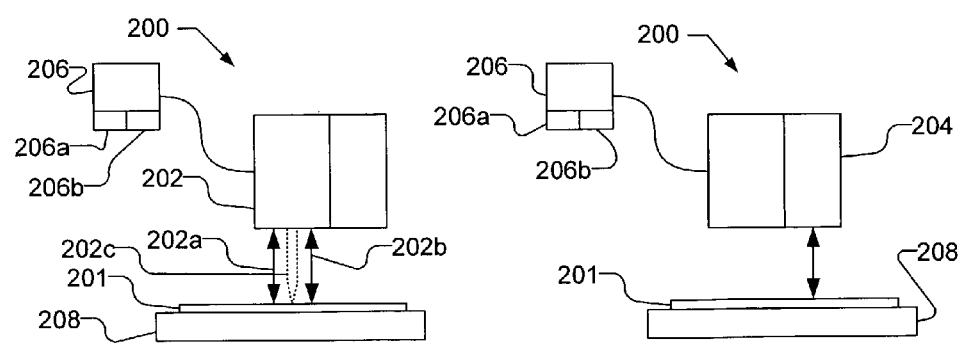
FIGS. 5A and 5B show a metrology apparatus that may be used in accordance with the present invention.

Thus, in accordance with the present invention, the height profile (or slope of the height profile) of a sample is measured, along with the thickness of the layer or layers on the sample surface at two or more locations in order to accurately level the sample. In one embodiment, for example, two metrology tools are used to measure the surface profile and the thickness of the layers. FIGS. 5A and 5B, for example, show a metrology apparatus 200 that may be used in accordance with the present invention. Metrology apparatus 200 includes a first metrology tool 202, such as a differential interferometer, with measurement and reference beams 202a and 202b operating in differential scanning mode. The metrology tool 202 alternatively may be a single point measurement tool, such as a contact profilometer or atomic force microscope (AFM), as indicated by the broken line 202c in FIG. 5A. The metrology tool 202 measures the slope of the height profile or the height profile of the sample 201, if metrology tool 202 is a differential interferometer or single point measurement tool, respectively. A second metrology tool 204 (FIG. 5B) that may be coupled to, part of, or separate from the first metrology tool 202 is used to measure the thickness of the overlying layer or layers on sample 201 at a plurality of points. The second metrology tool 204 may be, e.g., a reflectometer, ellipsometer, or any other tool that can measure the film thickness.

The metrology apparatus 200, i.e., both the first metrology tool 202 and the second metrology tool 204, is coupled to a processor 206, e.g., a workstation, a personal computer, or central processing unit, e.g., Pentium 4™ or other adequate computer system. The processor 206 includes a storage medium 206A, i.e., memory, for storing data provided by first and second metrology tools 202, 204 as well as a computer-usable medium 206B having computer-readable program code embodied therein for leveling a substrate, in accordance with the present invention. Generating code to level a substrate in accordance with the present invention is well within the abilities of those skilled in the art in light of the present disclosure. The processor 206 may be coupled to a stage 208 that holds the sample 201. The stage 208 is controlled, e.g., by the processor 206, to move the sample 201 relative to the metrology apparatus 200. Of course, if desired, the metrology apparatus 200 may move relative to the sample 201.

Figure 6:
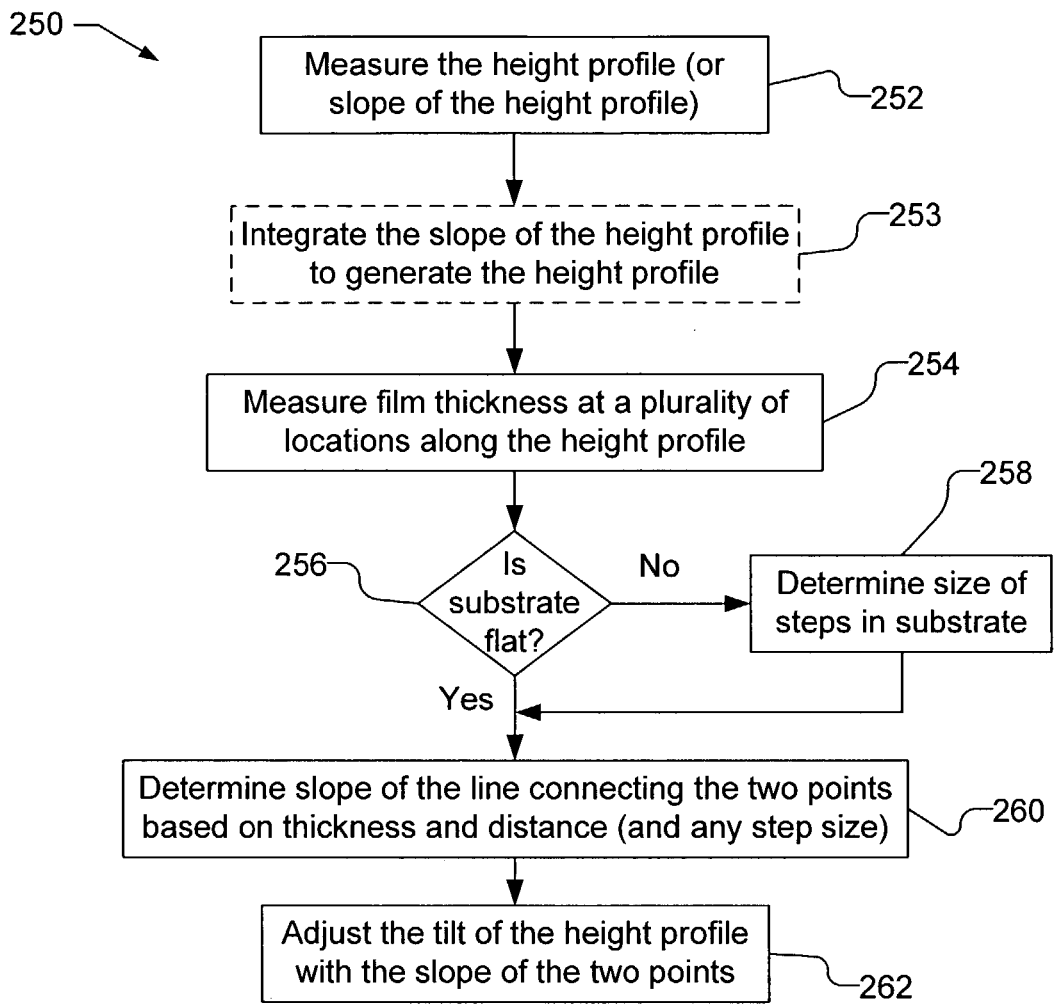
FIG. 6 is a flow chart illustrating a method of leveling a sample in accordance with the present invention.

FIG. 6 is a flow chart 250 illustrating a method of leveling a sample in accordance with the present invention. As shown in block 252, the height profile, or the slope of the height profile of a sample is measured using the first metrology tool 202 (FIG. 5A). If the slope of the height profile is measured, it is integrated to yield the height profile (block 253). As discussed above, if the step height is calculated based on an unleveled height profile (or even after leveling using known flat areas) significant tilting errors may occur.

Next, the thicknesses of the overlying layer or layers at two or more locations on the sample are measured, e.g., along the height profile (block 254). The thicknesses are measured, e.g., using the second metrology tool 204 (FIG. 5B). If the films are conductive, a conductive film measurement tool is used. A typical example might be an x-ray diffraction tool used to measure metal film thickness of one or more layers. A tool that measures metal resistance can also be used along with an assumed value of resistivity to calculate metal thickness. Typically, the resistivity is known with sufficient precision to make a resistance measurement and calculate thickness using an assumed resisitivity. For example, an eddy current probe may be used, such as the Mesac tool manufactured by Ulvac Technologies, Inc., located in Methuen, Mass. Other technologies are also known to precisely measure the metal thickness of films such as the MetaPulse 300 tool manufactured by Rudolph Technologies, Inc. of Flanders, N.J.

If the overlying films are transparent, an optical measurement tool is used, such as a spectroscopic reflectometer or an ellipsometer. Conductive films can also be measured using these technologies if they are sufficiently thin, e.g., less than approximately 60 nm. For example, the thicknesses of a multi-layer stack of transparent films can be measured using a NanoSpec 9300 manufactured by Nanometrics, Inc. of Milpitas, Calif.

If the thickness measurements are made in areas that have the same substrate height, e.g., the substrate is flat over the region including the two or more measurement locations, no further calculations need to be made and the measured thicknesses will be used to correct the tilt associated with the height profile (block 256). If, however, the substrate is not flat at the thickness measurement points, i.e., the thickness measurement points are made at points on the sample that have different substrate heights, the size of the steps between measurement points must be known in conjunction with the film thicknesses to correct the tilt associated with the height profile (block 258).

The height profile of the sample is then adjusted based on the thickness measurements. In one embodiment, the slope of the line between the thickness measurement points is determined based on the thickness at each point and the distance between the thickness measurement points and any step size (block 260). The slope of the line between the thickness measurements points is then used to adjust the tilt of the height profile (block 262).

For example, the thickness is measured at two locations along the height profile and then the slope of the height profile between these two points is adjusted until the slope of the height profile corresponds to the slope of the line between the two thickness locations. It should be understood that the slope of the height profile between the two thickness measurement locations is typically different than the slope of the height profile measured by a differential scan of a differential interferometer. The slope of the height profile generated by the differential interferometer must be integrated to obtain the height profile, after which the slope of the height between the two thickness measurement locations may be determined.

In another embodiment, the height profile may be adjusted without generating the slope of the thickness. For example, the height profile may be adjusted so that the difference in height at the thickness measurement points is the same as the difference in thickness at these locations.

Once the height profile is leveled, step heights can be calculated from the leveled height profile. Tilting errors should be essentially removed leaving only errors associated with the metrology hardware and technique.

Figure 7A:
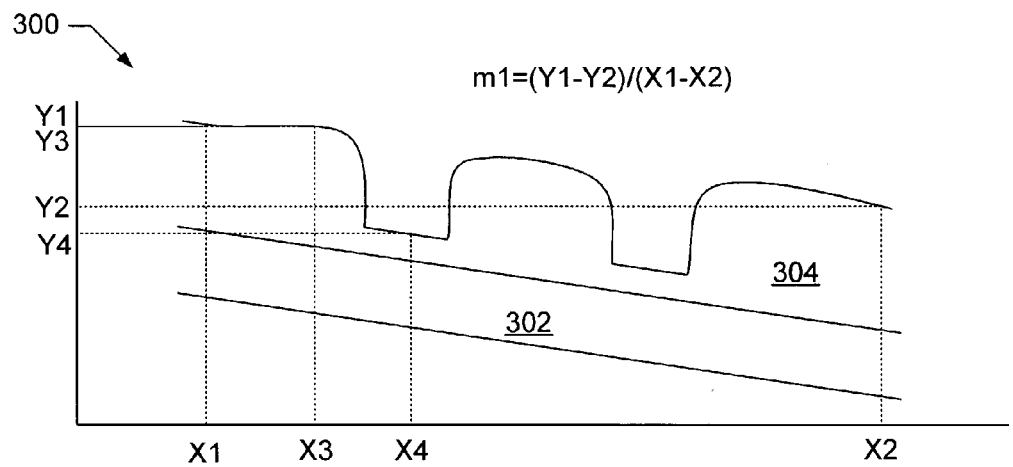
FIGS. 7A, 7B, and 7C graphically illustrate leveling a sample, in accordance with an embodiment of the present invention.
Figure 7B:
Figure 7C:
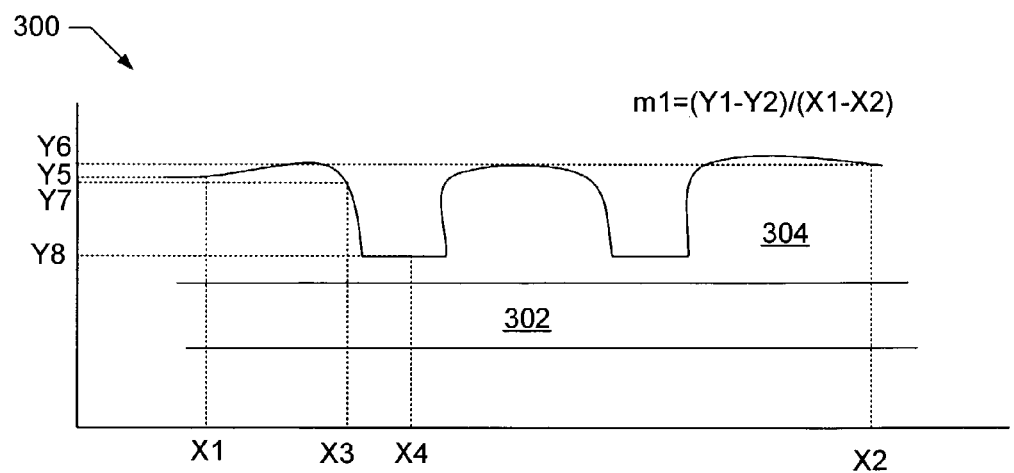

FIGS. 7A, 7B, and 7C, graphically illustrate leveling a sample, in accordance with an embodiment of the present invention. FIG. 7A shows a sample 300, which includes a substrate 302 and overlying film 304. The overlying film 304 may have one or more layers.

The sample is measured with a single point measurement tool or using a differential scan of a differential interferometer, to produce a height profile or slope of the height profile (as described in block 252 of FIG. 6). The height profile is illustrated in FIG. 7A as the top of sample 300.

In accordance with the present invention, the thickness of the overlying film 304 is measured at a plurality of locations, e.g., at locations X1 and X2. As illustrated in FIG. 7A, points (X1,Y1) and (X2,Y2) represent the length along the scan and the height of the profile at the two thickness measurement locations of a tilted height profile. The height values of the height profile are relative, not absolute, but the difference between the heights is absolute. The slope m1 of the height profile can be determined between points (X1,Y1) and (X2,Y2). Points (X3,Y3) and (X4,Y4) are the points that will be used to calculate the step height of the sample. The step height value of Y3–Y4, however, is not the correct step height value due to the large amount of tilting.

FIG. 7B shows a graph of a line through thickness values T1 and T2 at measurement points X1 and X2, respectively. The slope m2 of the line between the thickness at measurement points X1 and X2 is determined (as described in block 260 in FIG. 6). It will be common for the slope to be very close to zero. In this figure, the slope is exaggerated for clarity.

The height profile of FIG. 7A is adjusted so that the slope of a line through the measurement locations X1 and X2 is the same as the slope m2 of the line in FIG. 7B (as described in block 262 in FIG. 6). This may be accomplished mathematically in many different ways. By way of example, a line with a slope equal to m2−m1 is added to the tilted height profile from FIG. 7A. FIG. 7C illustrates a corrected height profile of sample 300, i.e., the height profile is adjusted to have the same slope m2 as the thickness measurement. Thus, as can be seen in FIG. 7C, the X positions X1, X2, X3, and X4 have new corresponding height positions Y5, Y6, Y7, and Y8, respectively.

In practice, it is not necessary to calculate the slope m1 of the height profile between the measurement points X1 and X2. The height profile may simply be adjusted so that the slope of the height profile matches the slope of the thickness. The height values of the height profile are relative, not absolute, but the difference between the heights is absolute. Moreover, if desired, the slope m2 of the thickness measurement need not be determined. For example, the difference in height at locations X1 and X2 of the height profile may be adjusted to be the same as the difference in thickness values at locations X1 and X2.

FIG. 7C shows a corrected height profile, i.e., the slope between points (X1,Y5) and (X2,Y6) has slope m2. Based on the corrected height profile, the step height can be more accurately determined as the difference in height between the two points (X3,Y7) and (X4,Y8), i.e., Y7–Y8.

It should be understood that more than two locations may be measured for thickness and a statistical value of average slope can be computed to adjust the height profile. In another embodiment, more than two thickness measurements are made and the slope of the height profile is adjusted at multiple locations. Adjusting the height profile at multiple locations has the potential advantage of eliminating some fraction of curvature errors, particularly if an adequately large number of thickness measurements are made.

In another embodiment, the height profile or the slope of the height profile is measured for an area, not just a line. Measuring the height profile or slope of the height profile over an area may be achieved using multiple scans of a single point measurement tool or differential interferometer executing a differential scan. A plurality of thickness measurements, e.g., three or more measurements, is then made of the film overlying the substrate.

For example, if three thickness measurements are made, the slope of the plane defined by the thickness measurement locations is then calculated based on the thicknesses and the distance between the three measurement locations. These three locations are then located on the height profile. The tilt of the area height profile is then adjusted so that the slope of the plane defined by the three locations is the same as the slope of the plane defined by the thickness measurements. If more than three locations are measured for thicknesses, some statistical value of average slope can be computed to adjust the area height profile. In another embodiment, multiple thickness measurements are made and the slope of the area height profile is adjusted at multiple locations. Adjusting the slope of the area height profile at multiple locations has the potential advantage of eliminating some fraction of curvature errors, particularly if an adequately large number of thickness measurements are made.

With the area height profile leveled, step heights can then be calculated from the height profile with the tilting error essentially removed leaving only errors associated with the metrology hardware and technique.

Although the present invention is illustrated in connection with specific embodiments for instructional purposes, the present invention is not limited thereto. Various adaptations and modifications may be made without departing from the scope of the invention. For example, various metrology tools may be used to perform the present invention. Moreover, the acts of the present invention may be performed in various orders, e.g., the thickness measurements may be made before, after or during the height profile measurements. Therefore, the spirit and scope of the appended claims should not be limited to the foregoing description.

What is claimed is:

1. A method comprising:
    determining a height profile of a sample that comprises a substrate with at least one overlying film;
    measuring the thickness of the overlying film at a plurality of measurement locations; and
    adjusting the tilt of the height profile of the sample using the measured thickness of the overlying film.

2. The method of claim 1, further comprising:
    determining the slope between the plurality of measurement locations based on the measured thickness and distance between the plurality of measurement locations; and
    wherein adjusting the tilt of the height profile of the sample uses the slope between the plurality of measurement locations.

3. The method of claim 1, wherein determining a height profile comprises measuring the height profile with a single point measurement tool.

4. The method of claim 1, wherein determining a height profile comprises:
    measuring the slope of the height profile using a differential scan with a differential interferometer; and integrating the slope of the height profile to determine the height profile.

5. The method of claim 1, wherein the plurality of measurement locations is two.

6. The method of claim 2, wherein the plurality of measurement locations is more than two and wherein determining the slope between the plurality of measurement locations comprises deriving a statistical value of the average slope between the plurality of measurement locations.

7. The method of claim 2, wherein determining the slope between the plurality of measurement locations is also based on a known height difference between the measurement locations.

8. The method of claim 2, wherein adjusting the tilt comprises modifying the slope of a line through the measurement locations in the height profile or the slope of the height profile so that it approximately matches the determined slope between the plurality of locations.

9. The method of claim 1, further comprising:
calculating the step height of a step in the sample as the difference in height between a first step height measurement location and a second step height measurement location using the adjusted height profile.

10. The method of claim 1, wherein the slope of the height profile is integrated to generate a height profile.

11. The method of claim 1, wherein the height profile is determined over an area of the sample, and wherein the measuring the thickness of the overlying film is performed at least at three measurement locations.

12. An apparatus comprising:
a first metrology tool that measures one of the height profile and the slope of the height profile of a sample that includes at least one film overlying a substrate;
a second metrology tool that measures the thickness of the at least one film, the thickness of the film being measured at a plurality of locations;
a computer system coupled to said first metrology tool to receive signals indicating one of the height profile and the slope of the height profile of the sample, the computer system coupled to said second metrology tool to receive signals indicating the thickness of the film being measured at each of the plurality of locations, said computer system having a computer-usable medium having computer-readable program code embodied therein for adjusting the height profile of the sample based on the measured thickness between the plurality of locations.

13. The apparatus of claim 12, further comprising computer-readable program code for integrating the slope of the height profile to generate the height profile.

14. The apparatus of claim 12, further comprising computer-readable program code for determining the slope of the thickness between the plurality of locations based on the measured thickness and distance between the plurality of locations, wherein adjusting the height profile of the sample is based on the slope of the thickness.

15. The apparatus of claim 12, wherein the first metrology tool is selected from a group comprising essentially of a contact profilometer, an atomic force microscope, and a differential interferometer.

16. The apparatus of claim 12, wherein the second metrology tool is selected from a group comprising essentially of a reflectometer, an ellipsometer, an x-ray diffraction tool, and a resistivity measurement tool.

17. The apparatus of claim 14, wherein determining the slope of the thickness comprises deriving a statistical value of the average slope between the plurality of measurement locations.

18. The apparatus of claim 14, wherein adjusting the height profile comprises modifying the slope of a line through the measurement locations in the height profile or the slope of the height profile so that it approximately matches the determined slope between the plurality of locations.

19. The apparatus of claim 12, further comprising computer-readable program code for calculating the step height of a step in the sample as the difference in height between a first step height measurement location and a second step height measurement location using the adjusted height profile.

20. The apparatus of claim 12, wherein said first metrology tool and said second metrology tool are integrated into a single tool.

* * * * *